US012626511B2

(12) United States Patent (10) Patent No.: US 12,626,511 B2

Kato et al. (45) Date of Patent: May 12, 2026

(54) DETECTION METHOD

(71) Applicant: NEC Corporation, Tokyo (JP)

(72) Inventors: Marina Kato, Tokyo (JP); Satoshi Terasawa, Tokyo (JP); Yohei Itou, Tokyo (JP); Natsuki Yui, Tokyo (JP)

(73) Assignee: NEC CORPORATION, Tokyo (JP)

( * ) Notice: Subject to any disclaimer, the term of this patent is extended or adjusted under 35 U.S.C. 154(b) by 548 days.

(21) Appl. No.: 17/802,397

(22) PCT Filed: Mar. 17, 2020

(86) PCT No.: PCT/JP2020/011763

§ 371 (c)(1),
(2) Date: Aug. 25, 2022

(87) PCT Pub. No.: WO2021/186564

PCT Pub. Date: Sep. 23, 2021

(65) Prior Publication Data

US 2023/0177837 A1     Jun. 8, 2023

(51) Int. Cl.
 *G06V 20/52* (2022.01)
 *A61B 5/11* (2006.01)
 *A61H 3/06* (2006.01)
 *G06V 40/10* (2022.01)

(52) U.S. Cl.
 CPC ............ *G06V 20/52* (2022.01); *A61B 5/1116* (2013.01); *A61H 3/061* (2013.01); *G06V 40/103* (2022.01)

(58) Field of Classification Search
 CPC .............................. G06V 20/52; A61B 5/1116
 See application file for complete search history.

(56) References Cited

U.S. PATENT DOCUMENTS

| | | | | |
|---|---|---|---|---|
| 10,452,892 | B2 * | 10/2019 | Hanai | .................... G06T 19/006 |
| 2014/0044305 | A1 * | 2/2014 | Scavezze | ........ H04M 1/724097 |
| | | | | 382/103 |
| 2018/0322334 | A1 * | 11/2018 | Tsuji | ........................ G06T 7/248 |
| 2019/0191103 | A1 * | 6/2019 | Takahashi | .............. H04N 23/80 |
| 2019/0370537 | A1 * | 12/2019 | Chen | ....................... G06V 10/34 |
| 2022/0165092 | A1 * | 5/2022 | Watanabe | .............. G08B 25/00 |

FOREIGN PATENT DOCUMENTS

| | | |
|---|---|---|
| CN | 106934991 A | 7/2017 |
| CN | 206610414 A | 11/2017 |
| JP | 2002-306218 5 | 10/2002 |
| JP | 2015159912 A * | 9/2015 |
| JP | 2017-108346 A | 6/2017 |

(Continued)

OTHER PUBLICATIONS

International Search Report for PCT Application No. PCT/JP2020/011763, mailed on Sep. 24, 2020.

(Continued)

*Primary Examiner* — Matthew C Bella

(74) *Attorney, Agent, or Firm* — Sughrue Mion, PLLC

(57) ABSTRACT

A detection system 100 of the present invention includes a position detection means 121 for detecting position information representing a position of a predetermined part of a person and a position of an accessory in a specific shape held by the person, and a separation detection means 122 for detecting that the accessory is separated from the person based on the position information.

20 Claims, 9 Drawing Sheets

(56) References Cited

FOREIGN PATENT DOCUMENTS

| | | | | |
|---|---|---|---|---|
| JP | 2019-016348 | A | | 1/2019 |
| JP | 2020034960 | A | * | 3/2020 |
| JP | 2020098474 | A | * | 6/2020 |
| JP | 7020931 | B2 | * | 2/2022 |
| WO | 2018/179472 | 6 | | 10/2018 |

OTHER PUBLICATIONS

Yadong Pan and Shoji Nishimura, "Multi-Person Pose Estimation with Mid-Points for Human Detection under Real-World Surveillance", The 5th Asian Conference on Pattern Recognition (ACPR 2019), Nov. 26-29, 2019, pp. 1-14.
JP Office Action for JP Application No. 2022-508667, mailed on Dec. 19, 2023 with English Translation.

* cited by examiner

Fig.2

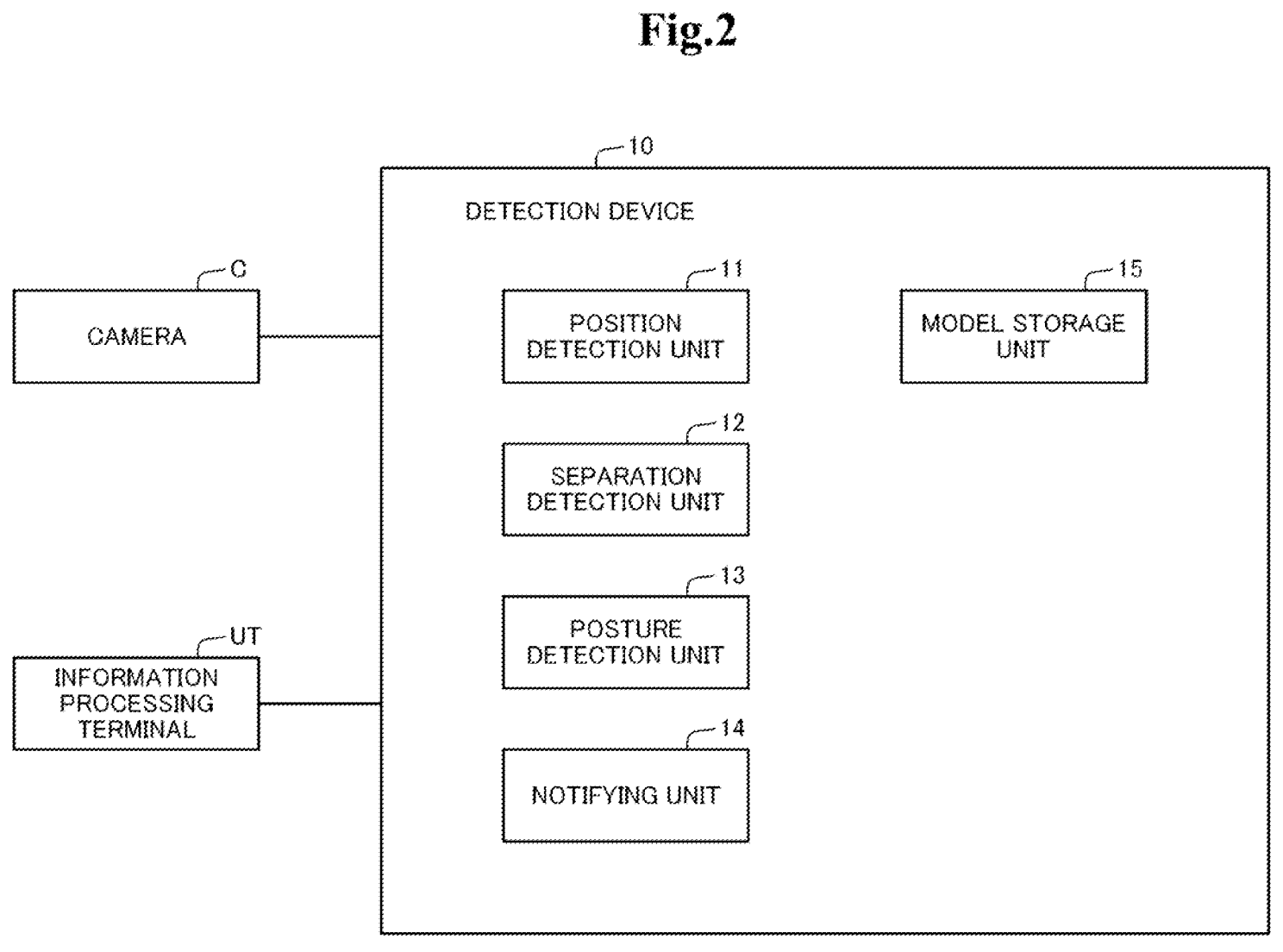

DETECTION DEVICE — 10

POSITION DETECTION UNIT — 11

SEPARATION DETECTION UNIT — 12

POSTURE DETECTION UNIT — 13

NOTIFYING UNIT — 14

MODEL STORAGE UNIT — 15

CAMERA — C

INFORMATION PROCESSING TERMINAL — UT

Fig.6

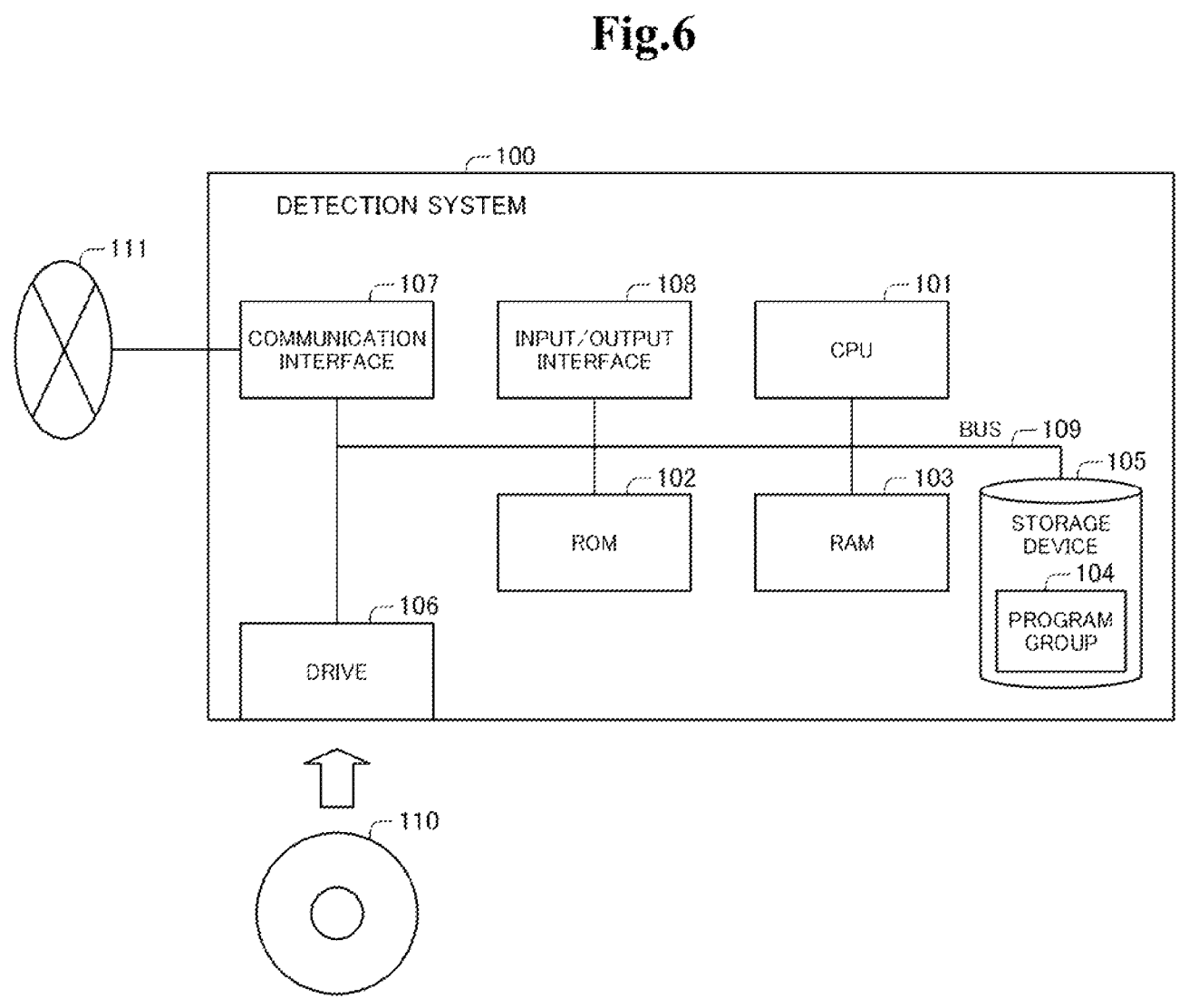

DETECTION SYSTEM — 100

COMMUNICATION INTERFACE — 107

INPUT/OUTPUT INTERFACE — 108

CPU — 101

BUS — 109

STORAGE DEVICE — 105

PROGRAM GROUP — 104

ROM — 102

RAM — 103

DRIVE — 106

— 110

— 111

DETECTION METHOD

This application is a National Stage Entry of PCT/JP2020/011763 filed on Mar. 17, 2020, the contents of all of which are incorporated herein by reference, in their entirety.

TECHNICAL FIELD

The present invention relates to a detection method, a detection system, and a program for detecting a situation of a person having an accessory.

BACKGROUND ART

Persons with physical disabilities may use various tools for assisting their motions in their daily life. For example, a visually impaired person uses a white cane as a walking assisting tool. A white cane is used for checking safety at the tip of the cane for a visually impaired person, collecting information required for walking, acknowledging that he/she is a visually impaired person by those around, and the like.

Meanwhile, a visually impaired person may be involved in a contact accident or a traffic accident. In particular, a white cane of a visually impaired person may come into contact with another person, a car, a bicycle, a train, or the like and may be involved in an accident. Therefore, when a white cane is used by a visually impaired person, there are may cases that a person does not hold the grip firmly in order not to be involved in an accident. As a result, an action that a white cane is separated from the hand of a visually impaired person may be caused.

Patent Literature 1: JP 2019-16348 A

Non-Patent Literature 1: Yadong Pan et & Shoji Nishimura, "Multi-Person Pose Estimation with Mid-Points for Human Detection under Real-World Surveillance", The 5th Asian Conference on Pattern Recognition (ACPR 2019), 26-29 Nov. 2019

SUMMARY

However, once a white cane is separated from the hand of a visually impaired person, it is difficult to pick it up thereafter. Accordingly, it is necessary to detect that a white cane is separated from the hand of a visually impaired person and that the visually impaired person is looking for a white cane, and to notify those around the person and assist the person.

In Patent Literature 1, a sensor for detecting acceleration is mounted on a white cane, and drop of the white cane is detected from the detected acceleration. However, it is difficult to detect that a white cane is separated from a visually impaired person more accurately only with the acceleration of the white cane, which may cause erroneous detection. Moreover, in that case, it is impossible to detect a motion of looking for an accessory such as a white cane by a person. This causes a problem that it is impossible to detect a situation that a person may be in trouble such as dropping a white cane or looking for a white cane. Such a problem may be caused in a situation of holding any accessory without being limited to a person having a white cane.

An object of the present invention is to provide a detection method, a detection system, and a program capable of solving the above-described problem, that is, a problem that it is impossible to detect a situation that a person having an accessory may be in trouble.

A detection method according to one aspect of the present invention is configured to include detecting position information representing a position of a predetermined part of a person and a position of an accessory in a specific shape held by the person, and based on the position information, detecting that the accessory is separated from the person.

Further, a detection system according to one aspect of the present invention is configured to include a position detection means for detecting position information representing a position of a predetermined part of a person and a position of an accessory in a specific shape held by the person, and a separation detection means for detecting that the accessory is separated from the person based on the position information.

Further, a program according to one aspect of the present invention is configured to cause an information processing device to realize a position detection means for detecting position information representing a position of a predetermined part of a person and a position of an accessory in a specific shape held by the person, and separation detection means for detecting that the accessory is separated from the person based on the position information.

With the configurations described above, the present invention can detect that an accessory is separated from a person with high accuracy.

BRIEF DESCRIPTION OF DRAWINGS

FIG. 2 is a block diagram illustrating a configuration of a detection device disclosed in FIG. 1.

FIG. 6 is a block diagram illustrating a hardware configuration of a detection system according to a second exemplary embodiment of the present invention.

EXEMPLARY EMBODIMENTS

First Exemplary Embodiment

Figure 1:
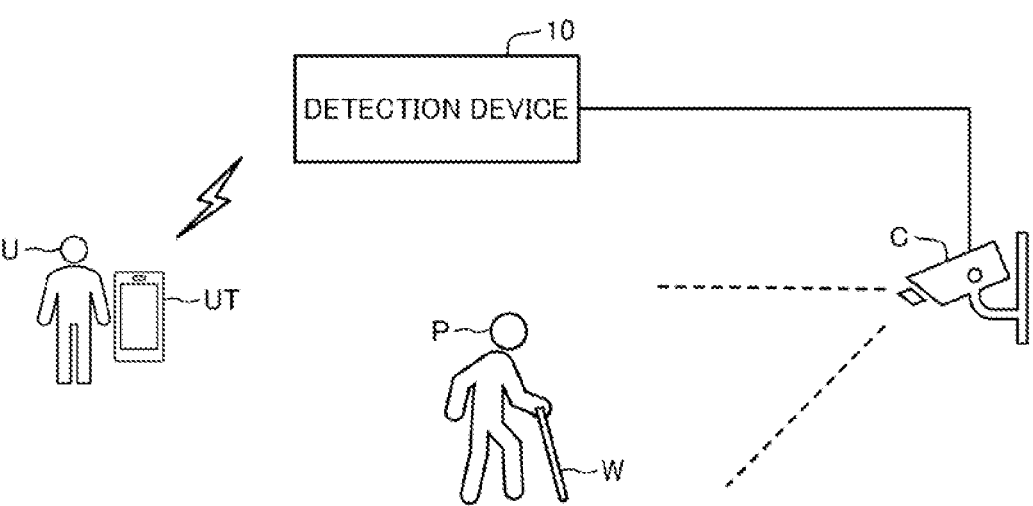
FIG. 1 illustrates the overall configuration of an information processing system according to a first exemplary embodiment of the present invention.

A first exemplary embodiment of the present invention will be described with reference to FIGS. 1 to 6. FIGS. 1 and 2 are diagrams for explaining a configuration of a detection system, and FIGS. 3 to 6 are illustrations for explaining processing operation performed by the detection system.

[Configuration]

A detection system of the present embodiment is used for detecting that a person P such as a visually impaired person releases a white cane W from a hand by dropping it or the like. Therefore, the detection system is used in a place where people visit such as a station, an airport, a shopping district, or a shopping mall. However, an object to be detected by the detection system is not limited to a white cane. Any accessory may be a detection object if it is an accessory in a specific shape held of by a predetermined part of the person P. For example, the detection system may be used for detecting glasses, a hat, a bag, or the like of the person P.

As illustrated in FIG. 1, the detection system is configured to include a camera C and a detection device 10. In a place where the detection system is used as described above, the detection device 10 is connected to an information processing terminal UT operated by a surveillant U who monitors the persons visiting such a place. The camera C is an imaging device for imaging the person P. The camera C may be newly installed for a detection system at a place where it is used, or may be one previously installed as a security camera or a surveillance camera. The camera C continuously images the user and transmits the captured images to the detection device 10, for example.

The detection device 10 is configured of one or a plurality of information processing devices each having an arithmetic device and a storage device. As illustrated in FIG. 2, the detection device 10 includes a position detection unit 11, a separation detection unit 12, a posture detection unit 13, and an informing unit 14. The respective functions of the position detection unit 11, the separation detection unit 12, the posture detection unit 13, and the informing unit 14 can be realized through execution, by the arithmetic unit, of a program for realizing the respective functions stored in the storage device. The detection device 10 also includes a model storage unit 15. The model storage unit 15 is configured of a storage device. Hereinafter, the respective constituent elements will be described in detail.

The position detection unit 11 (position detection means) acquires a captured image captured by the camera C. Then, the position detection unit 11 detects the person P shown in the captured image, and detects position information of a predetermined part of the person P. Specifically, the position detection unit 11 uses a posture estimation technique for detecting the skeleton of the person P as described in the Non-Patent Literature 1 to specify each part of the person P, and detects position information of each part. At that time, the position detection unit 11 uses a study model for detecting the skeleton of a person stored in the model storage unit 15 to detect position information of each part of the person P. As an example, as illustrated in the left drawing of FIG. 3, the position detection unit 11 detects position information of the wrists, elbows, shoulder, pelvis, knees, and ankles that are joints of the person P, and position information of the eyes, nose, and ears that are parts of the person P. Then, the position detection unit 11 of the present embodiment detects position information of a wrist in particular. However, the position detection unit 11 may detect position information of any part of the person P.

The position detection unit 11 detects position information of the white cane Was an accessory in a specific shape held by the person P from the captured image. For example, as illustrated in the left drawing of FIG. 3, the position detection unit 11 detects position information of a wrist part of the person P from the captured image as described above and also detects a white object in a long rod shape that is present near the wrist part as the white cane W, and detects position information of the white cane W. At that time, the position detection unit 11 detects position information of both ends of the white cane W in the longitudinal direction.

Then, the position detection unit 11 associates the position information of the wrist part of the person P with the position information of one end of both ends of the white cane W closer to the wrist with each other, and performs detection of these pieces of position information at certain time intervals with respect to newly captured images.

The position detection unit 11 does not necessarily detect position information of each part of the person P by using the posture estimation technique for detecting the skeleton of the person P as described above. The position detection unit 11 may detect position information of each part of the person by means of any method. Also, the position detection unit 11 does not necessarily detect position information of the white cane W by the above-described method, and may perform it by any method. For example, the position detection unit 11 may detect each piece of position information by using a sensor attached to a predetermined part of the person P such as a wrist or a sensor mounted on the white cane W, without using captured images. Note that when the position detection unit 11 detects position information of another accessory rather than the white cane W, the position detection unit 11 may extract an accessory in a captured image based on predetermined shape information of the accessory and detect position information of the accessory.

The separation detection unit 12 (separation detection means) calculates a distance D between a predetermined part of the person P and a predetermined part of the white cane W by using the position information of the person P and the position information of the white cane W detected as described above. Then, the separation detection unit 12 detects that the white cane W is separated from the person P based on the calculated distance D. For example, as illustrated in the right drawing of FIG. 3, the separation detection unit 12 calculates the distance D from the position information of the wrist of the person P and the position information of an end of the white cane W closer to the position of the wrist. Then, the separation detection unit 12 detects that the white cane W is separated from the person P when the calculated distance D is equal to or larger than a preset distance for a preset time or longer. As an example, the separation detection unit 12 detects that the white cane W is separated from the person P when the calculated distance D is 1 m or larger and such a distance D is continued for 5 seconds or longer.

However, the above-described method is an example. The separation detection unit 12 may detect that the white cane W is separated from the person P by another method. For example, the separation detection unit 12 may calculate a distance between the gravity center position of the person P and the gravity center position of the white cane W, and detect that the white cane W is separated from the person P according to such a distance.

The posture detection unit 14 (separation detection means) detects the posture of the person P after detecting that the white cane W is separated from the person P as described above. For example, the posture detection unit 14 acquires a captured image captured by the camera C, detects the person P shown in the captured image, and detects position information of a predetermined part of the person P. Specifically, the posture detection unit 14 uses a posture estimation technique for detecting the skeleton of the person P as described above to specify each part of the person P, and detects position information of each body part. For example, as illustrated in the left drawing of FIG. 4, the posture detection unit 14 detects position information of the wrists, elbows, shoulder, pelvis, knees, and ankles that are joints of the person P, and position information of the eyes, nose, and ears that are parts of the person P, as position information of the body parts of the person P. Then, the posture detection unit 14 detects the posture of the person P from the position relationship between the pieces of position information of the respective parts. For example, in the example of the left drawing of FIG. 4, from the position relationship between the joints of the person P, the posture detection unit 14 detects that the person P is in a bending posture, and detects that the person P is looking for the white cane W. Further, the posture detection unit 14 detects a posture such as the head position and the eye direction of the person P for example, and from the posture, detects that the person P is looking for the white cane W. Then, the posture detection unit 14 performs detection of the posture of the person P at constant time intervals with respect to newly captured images. The posture detection unit 14 may detect the motion of the person P from it. For example, when the posture of the person P is changed from the left drawing to the right drawing of FIG. 4, the posture detection unit 14 can detect that the person P moves to find the dropped white cane W.

As described above, when the notifying unit 15 (notifying means) detects that the white cane W is separated from the person P, the notifying unit 15 performs a notifying process to transmit notification information including that there is a person P who dropped the white board, to the information processing terminal UT of the surveillant U. At that time, the notifying unit 15 specifies the position of the camera C from the identification information of the camera C capturing the captured image from which the white cane W is separated from the person P is detected, and transmits the position information of the camera C as position information where the person P is present, to the information processing terminal UT as position information.

Further, the notifying unit 15 (second notifying means) detects the posture of the person P after detecting that the white cane W is separated from the person P as described above, and according to the posture and the motion, performs a notifying process (second notifying process) to transmit notification information to the information processing terminal UT of the surveillant U. For example, when the notifying unit 15 detects that the posture of the person P is a bending posture or detects that the person P moves to look for the white cane W, the notifying unit 15 transmits the fact that the person P is looking for the white cane W and position information that can be specified from the camera C that captured the captured image from which the fact is detected, to the information processing terminal UT as notification information.

Note that the notification information to be notified to the information processing terminal UT of the surveillant U by the notifying unit 15 is not limited to the information of the above-described content, and may be other information. Further, the notifying unit 15 does not necessarily notify notification information including the information that there is a person P who dropped the white cane W as described above to the information processing terminal UT. The notifying unit 15 may operate to notify only notification information including information that the person P is looking for the white cane W according to the posture of the person P thereafter.

[Operation]

Figure 5A:
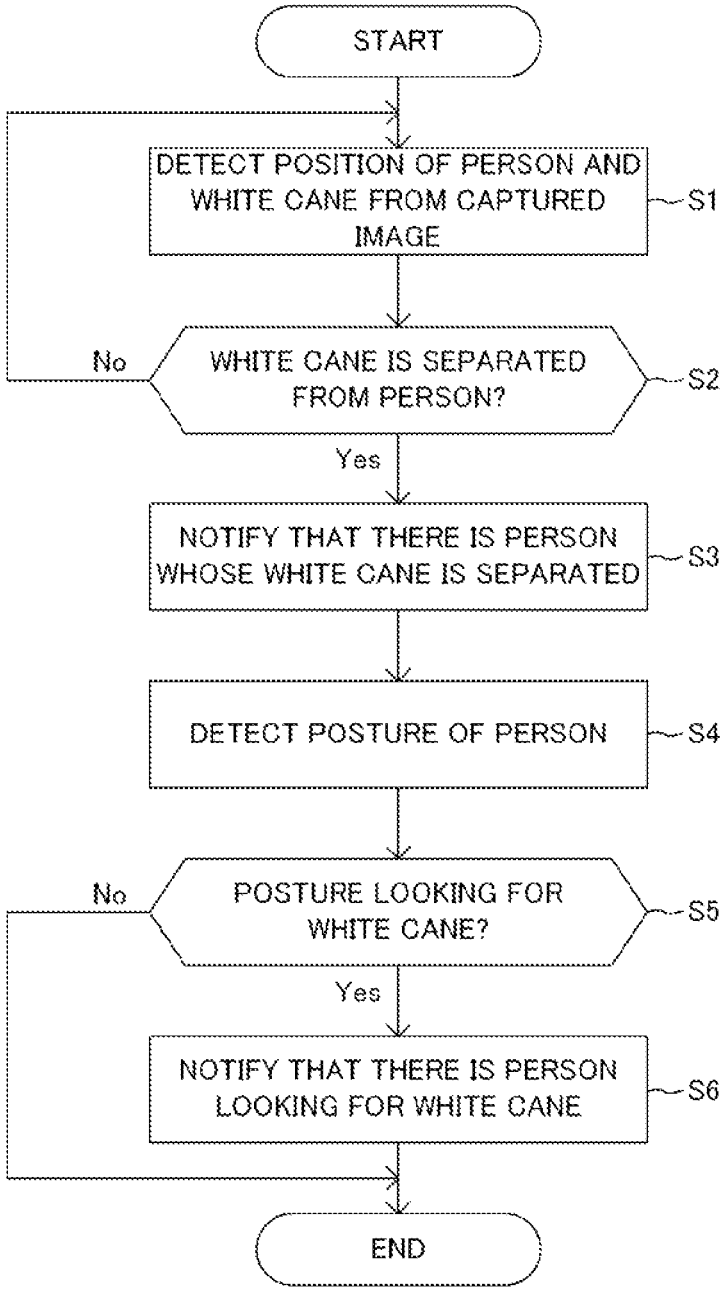
FIG. 5A is a flowchart illustrating an operation of the detection device disclosed in FIG. 1.

Next, operation of the detection device 10 described above will be described with mainly reference to the flowchart of FIG. 5A. First, the detection device 10 regularly acquires captured images captured by the camera C, and detects position information of the person P and the white cane W from the captured images (step S1). For example, the detection device 10 uses a posture estimation technique for detecting the skeleton of the person P to specify each part of the person P, and detects position information of each part. The detection device 10 also detects position information of the white cane W based on the shape and color characteristics of the white cane W. In particular, the detection device 10 detects the wrist position of the person P and an the end position of the white cane W.

Figure 3:
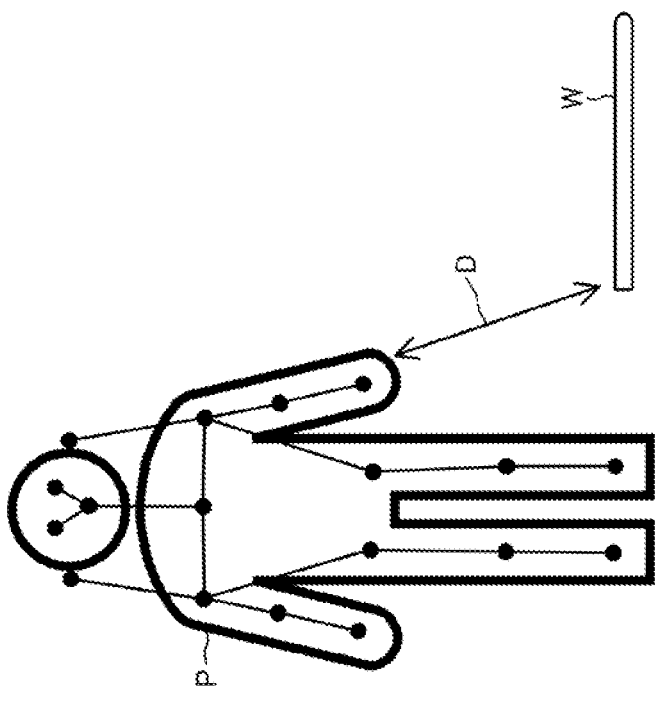
FIG. 3 illustrates a state of processing by the detection device disclosed in FIG. 1.
Figure 3:
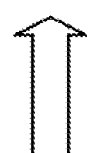
Figure 3:
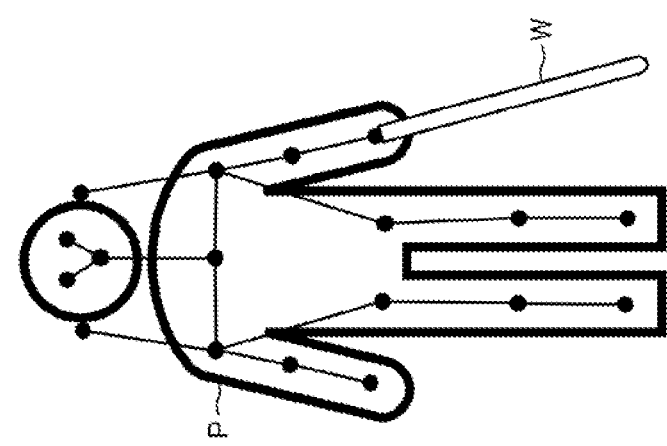

Then, the detection device 10 calculates the distance between the person P and the white cane W, and detects that the white cane W is separated from the person P according to the distance (Yes at step S2, step S3). For example, as illustrated in FIG. 3, the detection device 10 calculates the distance D between the wrist position of the person P and an end position of the white cane W, and when they are separated by a preset distance or more in a preset time or longer, the detection device 10 detects that the white cane W is separated from the person P. At that time, the detection device 10 may transmit notification information including the information that there is a person P who dropped the white cane W, to the information processing terminal UT of the surveillant U.

Figure 4:
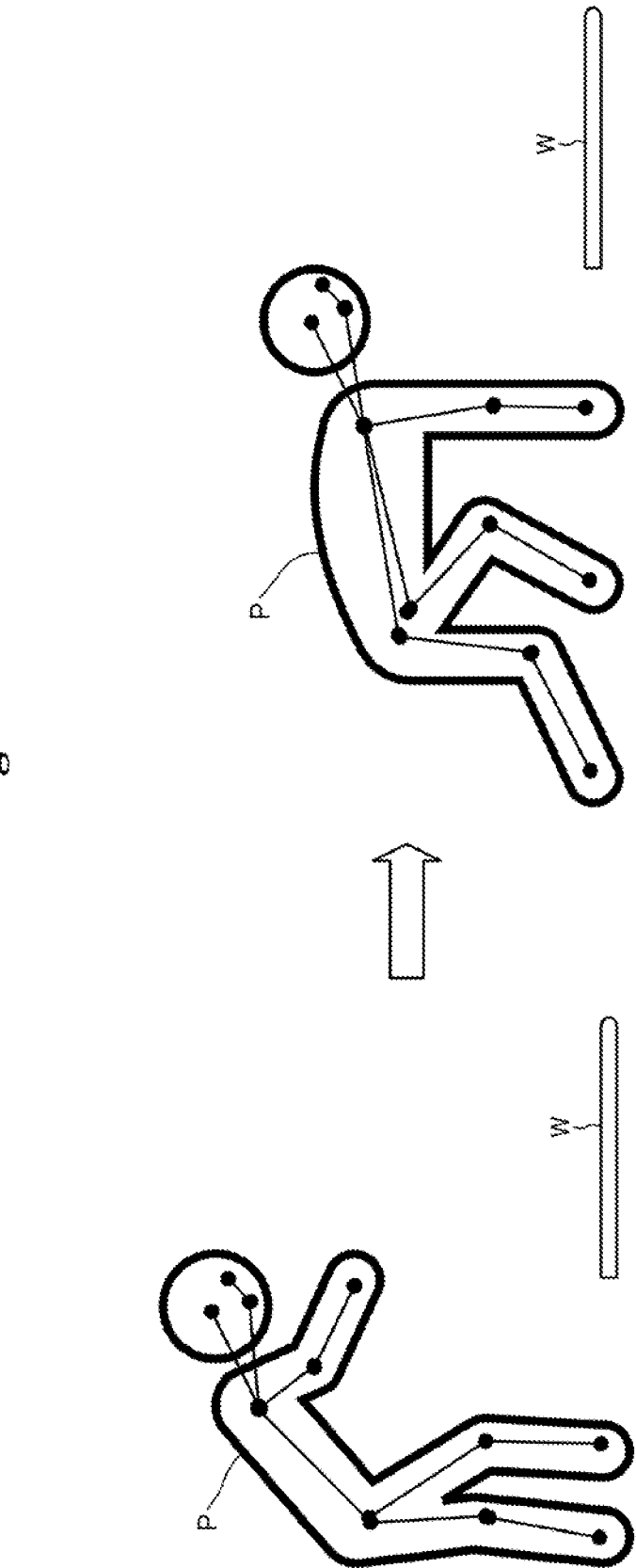
FIG. 4 illustrates a state of processing by the detection device disclosed in FIG. 1.

Then, the detection device 10 uses the captured image acquired after detecting that the white cane W is separated from the person P to detect the posture of the person P (step S4). For example, the detection device 10 uses a posture estimation technique for detecting the skeleton of the person P to specify each part of the person P, detects position information of each part, and detects the posture of the person P according to the position relationship between the parts. Then, as illustrated in FIG. 4 for example, when the detection device 10 detects that the person P is in a bending posture or the person P moves to look for the dropped white cane W from the position relationship between the joints of the person P (Yes at step S5), the detection device 10 notifies the information processing terminal UT of the surveillant U of the fact that there is a person P who is looking for the white cane W (step S6).

As described above, the present embodiment detects position information of a predetermined part of the person P and the white cane W, and detects that the white cane W is separated from the person P based on such position information. Therefore, it is possible to detect that the white cane W is separated from the person P accurately, and a prompt and appropriate assisting action can be taken with respect to the person P. Further, by detecting the posture of the person P who dropped the white cane W, it is possible to detect that the person P is looking for the white cane W accurately, and further, to take a prompt and appropriate assisting action for the person P.

<Modifications>

Figure 5B:
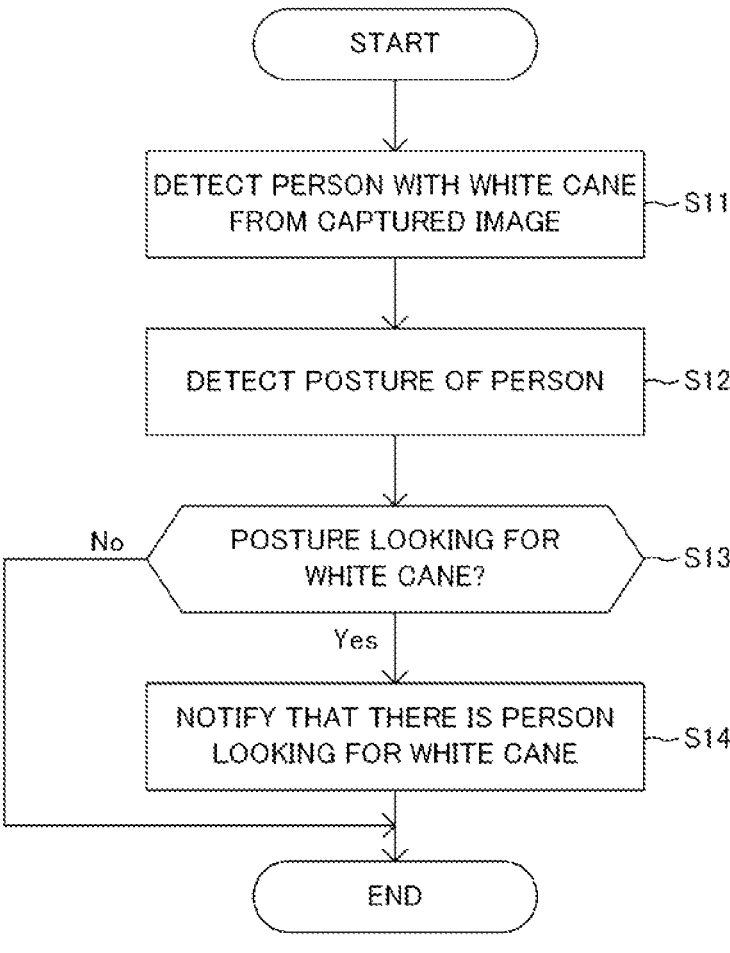
FIG. 5B is a flowchart illustrating another exemplary operation of the detection device disclosed in FIG. 1.

Next, another example of detecting that the person P is looking for the white cane W by the detection device 10 will be described with reference to the flowchart of FIG. 5B. First, the detection device 10 regularly acquires captured images captured by the camera C, detects position information of the person P and the white cane W from the captured images, and detects the person P holding the white cane W (step S11). For example, the detection device 10 uses a posture estimation technique for detecting the skeleton of the person P to specify each part of the person P, and detects position information of each part. The detection device 10 also detects position information of the white cane W based on the shape and color characteristics of the white cane W. In particular, the detection device 10 detects the wrist position of the person P and an end position of the white cane W, and detects the person P holding the white cane W by hand.

Note that the detection device 10 may not detect position information of each part of the person P and position information of the white cane W in a manner as described above. The detection device 10 may detect the person P with the white cane W by means of another method. For example, the detection device 10 may detect the person P with the white cane W by detecting the white cane W based on the shape and color characteristics of the white cane W and detecting the person P who is present near the white cane W from the feature amount of the object or motion. Further, in the present modification, the detection device 10 does not detect that the white cane W is separated from the person P such as the case where the person P dropped the white cane W, which is different from the above description.

Then, the detection device 10 uses the captured image acquired after detecting the person P having the white cane in hand to detect the posture of the person P (step S12). For example, the detection device 10 uses a posture estimation technique for detecting the skeleton of the person P to specify each part of the person P, detects position information of each part, and detects the posture of the person P according to the position relationship between the parts. Then, when the detection device 10 detects that the person P is in a bending posture as illustrated in the left drawing of FIG. 4 or the person P is in a posture of looking for something by crawling the floor as illustrated in the right drawing of FIG. 4 from, for example, the position relationship between the joints of the person P (Yes at step S13), the detection device 10 notifies the information processing terminal UT of the surveillant U of the fact that there is a person P who is looking for the white cane W (step S14).

As described above, in the present embodiment, the person P having the white cane W is detected first, and from the posture of the person P, it is determined that the person P is looking for the white cane W. Therefore, it is possible to accurately detect that the person P may be in trouble like looking for an accessory such as the white cane W, and to take a prompt and appropriate assisting action for the person P.

Second Exemplary Embodiment

Figure 7:
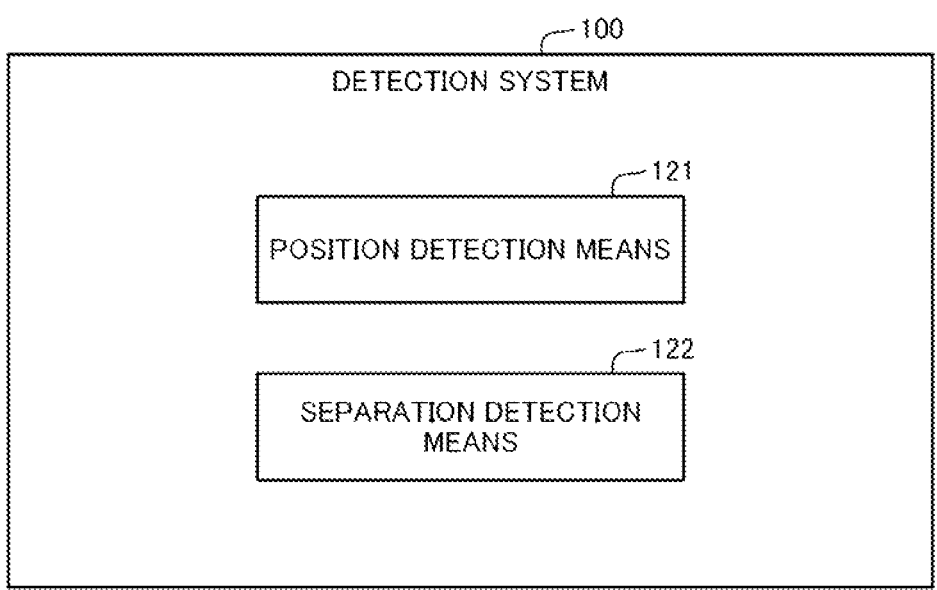
FIG. 7 is a block diagram illustrating a configuration of the detection system according to the second exemplary embodiment of the present invention.
Figure 8:
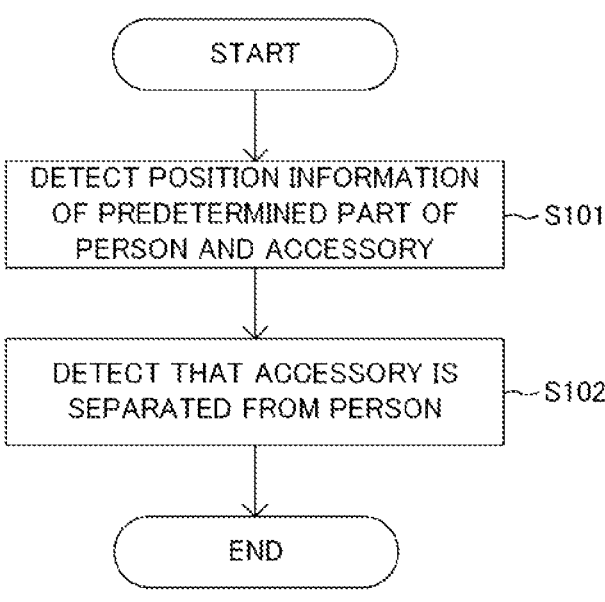
FIG. 8 is a flowchart illustrating an operation of the detection system according to the second exemplary embodiment of the present invention.

Next, a second exemplary embodiment of the present invention will be described with reference to FIGS. 6 to 8. FIGS. 6 and 7 are block diagrams illustrating a configuration of a detection system according to the second exemplary embodiment, and FIG. 8 is a flowchart illustrating an operation of the detection system. Note that the present embodiment shows the outlines of the configurations of the detection system and the detection method described in the above-described exemplary embodiment.

First, a hardware configuration of a detection system 100 in the present embodiment will be described with reference to FIG. 6. The detection system 100 is configured of a typical information processing device, having a hardware configuration as described below as an example.

Central Processing Unit (CPU) 101 (arithmetic device)
Read Only Memory (ROM) 102 (storage device)
Random Access Memory (RAM) 103 (storage device)
Program group 104 to be loaded to the RAM 103
Storage device 105 storing therein the program group 104
Drive 106 that performs reading and writing on a storage medium 110 outside the information processing device

Communication interface 107 connecting to a communication network 111 outside the information processing device
Input/output interface 108 for performing input/output of data
Bus 109 connecting the respective constituent elements The detection system 100 can construct, and can be equipped with, a position detection means 121 and a separation detection means 122 illustrated in FIG. 7 through acquisition and execution of the program group 104 by the CPU 101. Note that the program group 104 is stored in the storage device 105 or the ROM 102 in advance, and is loaded to the RAM 103 and executed by the CPU 101 as needed. Further, the program group 104 may be provided to the CPU 101 via the communication network 111, or may be stored on the storage medium 110 in advance and read out by the drive 106 and supplied to the CPU 101. However, the position detection means 121 and the separation detection means 122 may be constructed by dedicated electronic circuits for implementing such means.

Note that FIG. 6 illustrates an example of a hardware configuration of an information processing device that is the detection system 100. The hardware configuration of the information processing device is not limited to that described above. For example, the information processing device may be configured of part of the configuration described above, such as without the drive 106.

The detection system 100 executes the detection method illustrated in the flowchart of FIG. 8, by the functions of the position detection means 121 and the separation detection means 122 constructed by the program as described above.

As illustrated in FIG. 8, the detection system 100 executes the processing to detect position information representing a position of a predetermined part of a person and a position of an accessory in a specific shape held by the person (step S101), and based on the position information, detect that the accessory is separated from the person (step S102).

Since the present invention is configured as described above, the present invention detects position information of a predetermined part of a person and an accessory, and based on the position information, detects that the accessory is separated from the person. Therefore, it is possible to accurately detect that a white cane is separated from the person, that is, to accurately detect a situation that a person may be in trouble, and to take a prompt and appropriate assisting action for the person.

Note that the program described above can be supplied to a computer by being stored in a non-transitory computer-readable medium of any type. Non-transitory computer-readable media include tangible storage media of various types. Examples of non-transitory computer-readable media include magnetic storage media (for example, flexible disk, magnetic tape, and hard disk drive), magneto-optical storage media (for example, magneto-optical disk), a CD-ROM (Read Only Memory), a CD-R, a CD-R/W, and semiconductor memories (for example, mask ROM, PROM (Programmable ROM), EPROM (Erasable PROM), a flash ROM, and a RAM (Random Access Memory)). Note that the program may be supplied to a computer by being stored in a transitory computer-readable medium of any type. Examples of transitory computer-readable media include electric signals, optical signals, and electromagnetic waves. A transitory computer-readable medium can be supplied to a computer via a wired communication channel such as a wire and an optical fiber, or a wireless communication channel.

While the present invention has been described with reference to the exemplary embodiments described above, the present invention is not limited to the above-described embodiments. The form and details of the present invention can be changed within the scope of the present invention in various manners that can be understood by those skilled in the art. Further, at least one of the functions of the position detection means 121 and the separation detection means 122 described above may be carried out by an information processing device provided and connected to any location on the network, that is, may be carried out by so-called cloud computing.

<Supplementary Notes>

The whole or part of the exemplary embodiments disclosed above can be described as the following supplementary notes. Hereinafter, outlines of the configurations of a detection method, a detection system, and a program according to the present invention will be described. However, the present invention is not limited to the configurations described below.

(Supplementary Note 1)

A detection method comprising:

detecting position information representing a position of a predetermined part of a person and a position of an accessory in a specific shape held by the person; and based on the position information, detecting that the accessory is separated from the person.

(Supplementary Note 2)

The detection method according to supplementary note 1, further comprising detecting the position information of the predetermined part of the person and the accessory by detecting a skeleton of the person from a captured image in which the person is captured.

(Supplementary Note 3)

The detection method according to supplementary note 1 or 2, further comprising detecting that the accessory is separated from the person by a preset distance or more.

(Supplementary Note 4)

The detection method according to any of supplementary notes 1 to 3, further comprising detecting that the accessory is separated from the person for a preset time or more.

(Supplementary Note 5)

The detection method according to any of supplementary notes 1 to 4, further comprising when detecting that the accessory is separated from the person, performing a preset notifying process.

(Supplementary Note 6)

The detection method according to any of supplementary notes 1 to 5, further comprising detecting a posture of the person after it is detected that the accessory is separated from the person.

(Supplementary Note 7)

The detection method according to supplementary note 6, further comprising detecting the posture of the person by detecting a skeleton of the person from a captured image in which the person is captured after it is detected that the accessory is separated from the person.

(Supplementary Note 8)

The detection method according to supplementary note 6 or 7, further comprising detecting a motion of the person on a basis of the posture of the detected person.

(Supplementary Note 9)

The detection method according to supplementary note 7 or 8, further comprising performing a preset second notifying process on a basis of the detected posture of the person.

(Supplementary Note 10)

The detection method according to any of supplementary notes 1 to 9, wherein the accessory is a rod-shaped body having a predetermined length.

(Supplementary Note 11)

The detection method according to supplementary note 10, wherein the accessory is a white cane.

(Supplementary Note 12)

A detection system comprising:

position detection means for detecting position information representing a position of a predetermined part of a person and a position of an accessory in a specific shape held by the person; and separation detection means for detecting that the accessory is separated from the person based on the position information.

(Supplementary Note 13)

The detection system according to supplementary note 12, wherein the position detection means detects the position information of the predetermined part of the person and the accessory by detecting a skeleton of the person from a captured image in which the person is captured.

(Supplementary Note 14)

The detection system according to supplementary note 12 or 13, wherein the separation detection means detects that the accessory is separated from the person by a preset distance or more.

(Supplementary Note 15)

The detection system according to any of supplementary notes 12 to 14, wherein the separation detection means detects that the accessory is separated from the person for a preset time or more.

(Supplementary Note 16)

The detection system according to any of supplementary notes 12 to 15, further comprising notifying means for, when detecting that the accessory is separated from the person, performing a preset notifying process.

(Supplementary Note 17)

The detection system according to any of supplementary notes 12 to 16, further comprising posture detection means for detecting a posture of the person after it is detected that the accessory is separated from the person.

(Supplementary Note 18)

The detection system according to supplementary note 17, wherein the posture detection means detects the posture of the person by detecting a skeleton of the person from a captured image in which the person is captured after it is detected that the accessory is separated from the person.

(Supplementary Note 19)

The detection system according to supplementary note 17 or 18, wherein the posture detection means detects a motion of the person on a basis of the posture of the detected person.

(Supplementary Note 20)

The detection system according to supplementary note 18 or 19, further comprising second notifying means for performing a preset second notifying process on a basis of the detected posture of the person.

(Supplementary Note 21)

A computer-readable medium storing thereon a program for causing an information processing device to realize:

position detection means for detecting position information representing a position of a predetermined part of a person and a position of an accessory in a specific shape held by the person; and separation detection means for detecting that the accessory is separated from the person based on the position information.

(Supplementary Note 21.1)

The computer-readable medium according to supplementary note 21, the medium storing thereon the program for causing the information processing device to further realize notifying means for, when detecting that the accessory is separated from the person, performing a preset notifying process.

(Supplementary Note 22)

The computer-readable medium according to supplementary note 21, the medium storing thereon the program for causing the information processing device to further realize posture detection means for detecting a posture of the person after it is detected that the accessory is separated from the person.

(Supplementary Note 22.1)

The computer-readable medium according to supplementary note 21, the medium storing thereon the program for causing the information processing device to further realize second notifying means for performing a preset second notifying process on a basis of the detected posture of the person.

(Supplementary Note A1)

A detection method comprising:

detecting a person having an accessory;

detecting a posture of the person thereafter; and based on the detected posture of the person, detecting that the person takes a preset specific posture.

(Supplementary Note A2)

The detection method according to supplementary note A1, further comprising detecting the posture of the person by detecting a skeleton of the person from a captured image in which the person is captured.

(Supplementary Note A3)

The detection method according to supplementary note A1 or A2, further comprising based on the detected posture of the person, detecting that the person takes a posture to look for the accessory as the specific posture.

(Supplementary note A4)

The detection method according to any of supplementary notes A1 to A3, further comprising when detecting that the person takes the specific posture, performing a preset notifying process.

REFERENCE SIGNS LIST 10 detection device
11 position detection unit 12 separation detection unit
13 posture detection unit
14 notifying unit
15 model storage unit
C camera
P person
U surveillant
UT information processing terminal
100 detection system
101 CPU
102 ROM
103 RAM
104 program group
105 storage device
106 drive
107 communication interface
108 input/output interface
109 bus
110 storage medium
111 communication network
121 position detection means
122 separation detection means

What is claimed is:

1. A detection method comprising:

detecting position information representing a position of a predetermined part of a person and a position of an accessory in a specific shape held by the person;

based on the position information, detecting that the accessory is separated from the person;

detecting a posture of the person after it is detected that the accessory is separated from the person and detecting that the person is looking for the accessory based on the posture; and transmitting notification information to an information processing terminal, the notification information including the posture of the person, wherein the detection method further comprises detecting that the accessory is separated from the person for a preset time or more.

2. The detection method according to claim 1, further comprising detecting the position information of the predetermined part of the person and the accessory by detecting a skeleton of the person from a captured image in which the person is captured.

3. The detection method according to claim 1, further comprising detecting that the accessory is separated from the person by a preset distance or more.

4. The detection method according to claim 1, further comprising when detecting that the accessory is separated from the person, performing a preset notifying process.

5. The detection method according to claim 1, further comprising detecting a posture of the person after it is detected that the accessory is separated from the person.

6. The detection method according to claim 5, further comprising detecting the posture of the person by detecting a skeleton of the person from a captured image in which the person is captured after it is detected that the accessory is separated from the person.

7. The detection method according to claim 5, further comprising detecting a motion of the person on a basis of the posture of the detected person.

8. The detection method according to claim 6, further comprising performing a preset second notifying process on a basis of the detected posture of the person.

9. The detection method according to claim 1, wherein the accessory is a rod-shaped body having a predetermined length.

10. The detection method according to claim 9, wherein the accessory is a white cane.

11. An information processing device comprising:

at least one memory configured to store instructions; and at least one processor configured to execute instructions to:

detect position information representing a position of a predetermined part of a person and a position of an accessory in a specific shape held by the person;

detect that the accessory is separated from the person based on the position information;

detect a posture of the person after it is detected that the accessory is separated from the person and detect that the person is looking for the accessory based on the posture; and transmit notification information to an information processing terminal, the notification information including the posture of the person, wherein the at least one processor is configured to execute the instructions to detect that the accessory is separated from the person for a preset time or more.

12. The information processing device according to claim 11, wherein the at least one processor is configured to execute the instructions to detect the position information of the predetermined part of the person and the accessory by detecting a skeleton of the person from a captured image in which the person is captured.

13. The information processing device according to claim 11, wherein the at least one processor is configured to execute the instructions to detect that the accessory is separated from the person by a preset distance or more.

14. The information processing device according to claim 11, wherein the at least one processor is configured to execute the instructions to, when detecting that the accessory is separated from the person, perform a preset notifying process.

15. The information processing device according to claim 11, wherein the at least one processor is configured to execute the instructions detect a posture of the person after it is detected that the accessory is separated from the person.

16. The information processing device according to claim 15, wherein the at least one processor is configured to execute the instructions to, detect the posture of the person by detecting a skeleton of the person from a captured image in which the person is captured after it is detected that the accessory is separated from the person.

17. The information processing device according to claim 16, wherein the at least one processor is configured to execute the instructions to perform a preset second notifying process on a basis of the detected posture of the person.

18. A non-transitory computer-readable medium storing thereon a program comprising instructions for causing an information processing device to execute processing to:

detect position information representing a position of a predetermined part of a person and a position of an accessory in a specific shape held by the person;

detect that the accessory is separated from the person based on the position information;

detect a posture of the person after it is detected that the accessory is separated from the person and detect that the person is looking for the accessory based on the posture; and transmit notification information to an information processing terminal, the notification information including the posture of the person, wherein the instructions further cause the information processing device to execute processing to detect that the accessory is separated from the person for a preset time or more.

19. The detection method according to claim 1, further comprising detecting that the person is looking for the accessory based on the posture of bending.

20. The detection method according to claim 1, further comprising detecting that the person is looking for the accessory based on the posture of a head position and an eye direction of the person.

* * * * *